(12) United States Patent
Westerbeck

(10) Patent No.: US 6,406,452 B1
(45) Date of Patent: Jun. 18, 2002

(54) BLADDER CATHETER FOR HYPERTHERMIA SYSTEM

(75) Inventor: Todd L. Westerbeck, Burnsville, MN (US)

(73) Assignee: First Circle Medical, Inc., Minneapolis, MN (US)

( * ) Notice: Subject to any disclaimer, the term of this patent is extended or adjusted under 35 U.S.C. 154(b) by 0 days.

(21) Appl. No.: 09/334,224

(22) Filed: Jun. 16, 1999

(51) Int. Cl.[7] ............................................... A61M 37/00
(52) U.S. Cl. ....................................... 604/6.13; 604/113
(58) Field of Search ........................... 604/30, 31, 4.01, 604/5.01, 5.02, 5.03, 5.04, 6.08, 6.09, 6.1, 6.11, 6.12, 6.13

(56) References Cited

U.S. PATENT DOCUMENTS 4,298,006 A    11/1981  Parks
5,391,142 A     2/1995  Sites et al.

OTHER PUBLICATIONS

"Extracorporeal Whole Body Hyperthermia," First Circle Medical, Inc., Doc. No. 1600002, 1999.

*Primary Examiner*—Manuel Mendez
(74) *Attorney, Agent, or Firm*—Popovich & Wiles, P.A.

(57) ABSTRACT

The invention provides a hyperthermia system comprising a catheter having an elongate body having a distal end and having a proximal end; a first temperature sensor located proximate the distal tip; and an inflatable cuff mounted distal of said first temperature sensor.

6 Claims, 3 Drawing Sheets

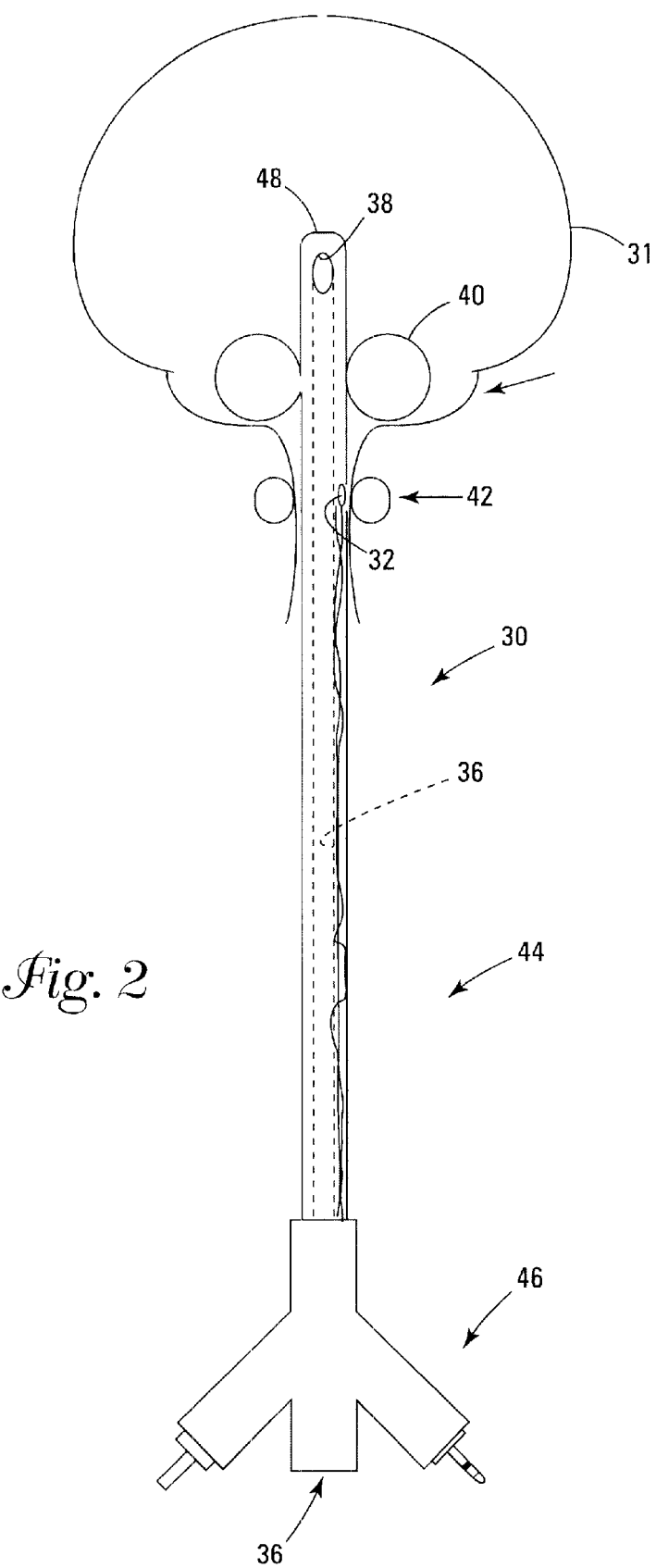

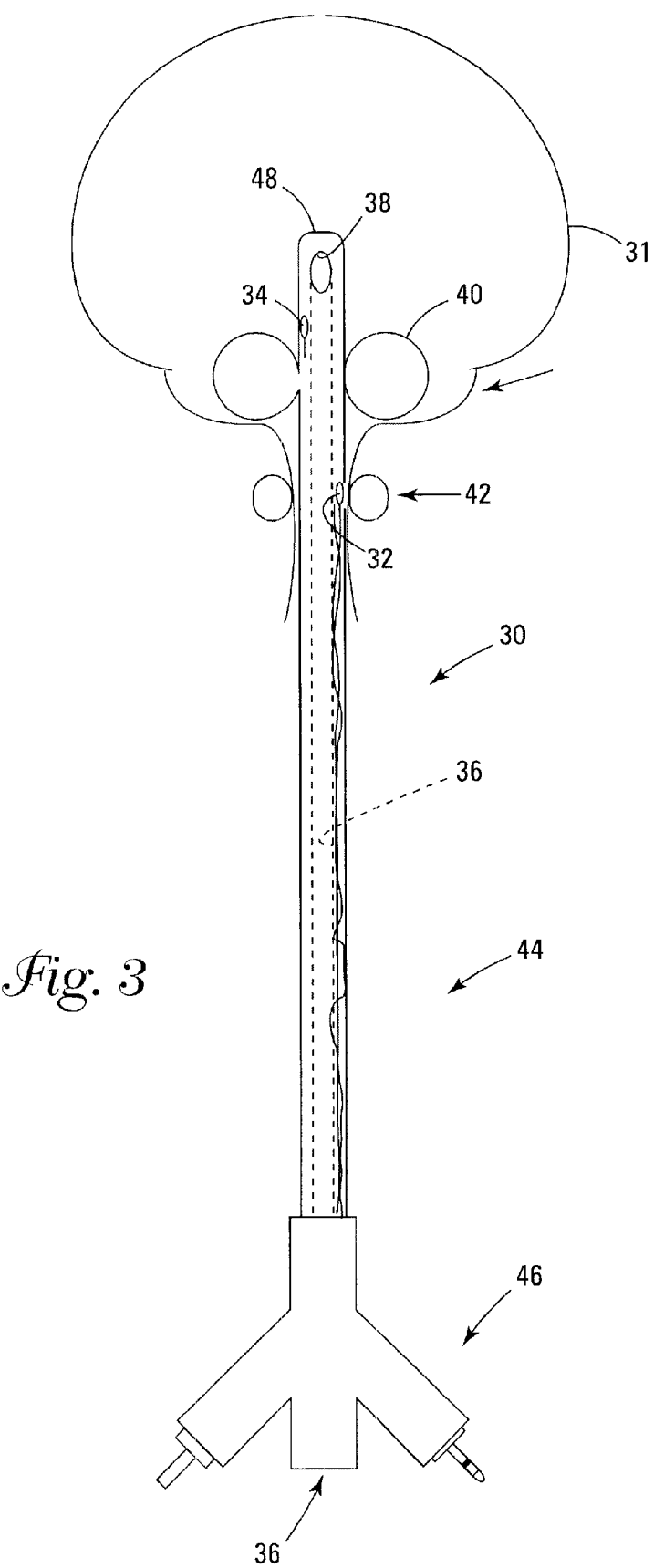

BLADDER CATHETER FOR HYPERTHERMIA SYSTEM

FIELD OF THE INVENTION

The present invention relates generally to catheters for monitoring body temperature and more particularly to a device for use in hyperthermia systems during patient treatment.

BACKGROUND OF THE INVENTION

Both whole body hyperthermia and local hyperthermia are procedures known in the art. Whole body hyperthermia is a disease treatment technique or therapy that has been used to treat a number of diseases. In operation, blood is removed from the body and heated externally to a target temperature and then returned to the body. Various treatment protocols have been proposed and several studies have been directed to assessing the efficacy of the therapy for several disease indications. Suitable structures for carrying out whole body hyperthermia are known from U.S. Pat. No. 5,391,192 to Sites et al., incorporated herein by reference. A microprocessor-based hyperthermia is known from the Optichem SLH 100 system. Experimentation has also been performed with conventional perfusion devices. Although the efficacy of the therapy is now established, there is a continuing need to improve the devices used to carry out this procedure. For example, efficacy is improved with accurate knowledge and control of body temperature.

The present invention improves the ability to monitor and control the blood and body temperature. An improved temperature monitoring device is especially well suited to whole body hyperthermia, but may be useful in other patient care settings as well.

SUMMARY OF THE INVENTION

A catheter is described in the context of a whole body hyperthermia system. However, this use is illustrative and should not be taken as limiting the invention. In use, the catheter is suspended in the bladder of the patient. A cuff on the catheter inflates after the catheter is inserted in the bladder to assist in positioning and securing the catheter. The catheter has a temperature sensor proximal of the inflatable cuff to measure body temperature at the urinary sphincter muscle. The sensor is located relative to the cuff a distance known to generally correspond to the typical distance between the bladder and the sphincter muscle in humans. This distance is known to be approximately the same amongst humans regardless of size.

In an alternative embodiment, a second temperature sensor is placed distal of the inflatable cuff and thus monitors the temperature of the urine pool in the bladder. Each of the measurements from the first and second temperature sensors has a different time constant depending on the volume of urine in the bladder, and the level of perfusion in the sphincter. Data from these two sensors, the differences between the readings, and the time-dependent variation of these two sensors can contribute to the overall efficacy of the device.

BRIEF DESCRIPTION OF THE DRAWING

An exemplary version of the bladder catheter is shown in the figures in which like reference numerals refer to equivalent structure throughout, and wherein:

FIG. 2 is a cross-section of an exemplary temperature catheter having a temperature sensor positioned at the urinary sphincter muscle with the aid of an inflatable cuff that engages the bladder wall; and FIG. 3 is a cross-section of an alternate embodiment of an exemplary temperature catheter having two temperature sensors, one of which is positioned at the urinary sphincter muscle with the aid of an inflatable cuff the engages the bladder wall and the second of which is positioned in the urine pool.

DETAILED DESCRIPTION

Figure 1:
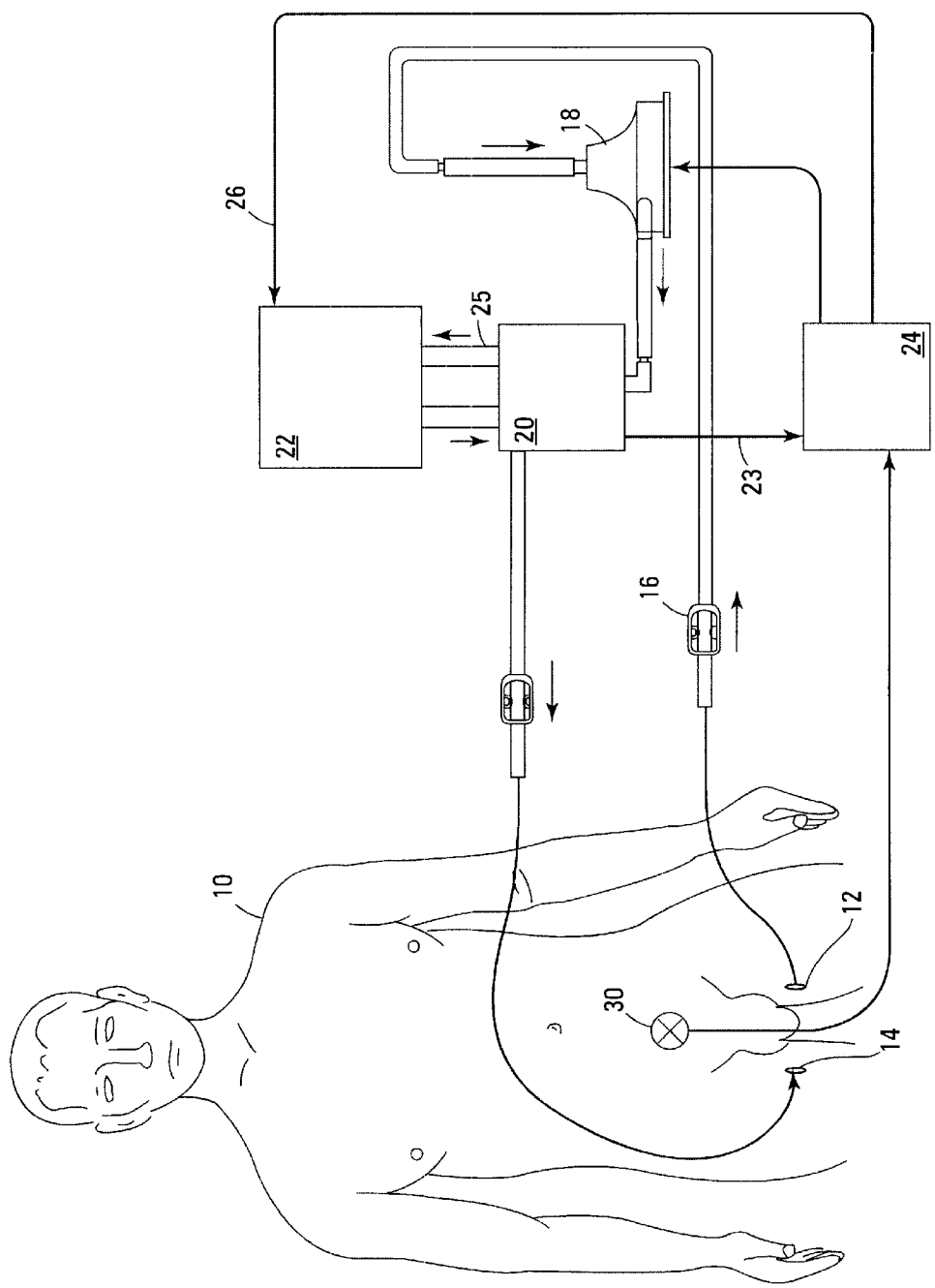
FIG. 1 is a schematic diagram of a simplified hyperthermia system.

FIG. 1 shows a patient 10 undergoing a perfusion treatment or whole body hyperthermia. Blood is withdrawn from a first cutdown 12 in the leg. Through extracorporeal transport, the blood is returned to another cutdown 14 in the other leg. Venous to venous transport is preferred. Connections to the patient are controlled by conventional clamps as depicted by clamp 16. The blood is moved through the system by a blood pump 18 of conventional construction. The blood is heated in a heat exchanger 20 placed in the perfusion circulation system. In this particular system, a remote heated water supply 22 supplies heated water to the heat exchanger 20 via connections 25.

A computer-based controller 24 receives temperature information from the heat exchanger 20 via connection 23 and supplies temperature control information to the heated water supply 22 via connection 26. The controller 24 may control water temperature using either open loop or closed loop control methods.

The controller 24 also receives body temperature information from the bladder probe 30, located within the patient's body. The controller 24 adjusts the temperature of the water in the heat exchanger 20 by providing control information to the water supply 22 via connection 26, thereby selectively controlling the temperature of the blood to achieve the hyperthermic conditions prescribed by protocol.

FIG. 2 shows a bladder temperature probe 30 having an elongate body 44 and terminating in a proximal end 46 and further having a distal tip 48 and a first temperature sensor 32, which may be of any conventional type, including thermistors, thermocouples or other solid state temperature sensors. A drainage lumen 36 communicates with a distal opening 38 to allow fluid to be withdrawn from the bladder 31 or to allow fluid, such as saline, to be infused into the bladder. An inflatable distal cuff 40 positions the catheter and prevents its removal from the bladder while the cuff is inflated. The sensor 32 and the inflatable cuff are spaced and oriented such that when the inflatable cuff 40 holds the probe 30 in position in the patient's bladder 31, the sensor 32 is located proximal of the urinary sphincter muscle 42. In a human, the distance between the sphincter muscle and the neck of bladder is known to be about 1.39 inches for males and about 0.79 inches for females. Temperature information gathered at this site from the surrounding tissue is likely to be reliable and somewhat less subject to rapid fluctuation than a temperature reading taken from other locations, such as the urine pool.

In an alternate embodiment, illustrated in FIG. 3, the catheter carries a second temperature sensor 34. In practice, the cuff positions the second temperature sensor 34 in the bladder urine or fluid pool while the first sensor 32 is located adjacent the musculature near the sphincter 42. It is expected that the two sensors will vary in measured temperature as the effective time constants for the two locations differ. These two temperatures and relative rates of their variation contribute to the efficacy of body temperature control.

Although the invention has been shown in the context of whole body hyperthermia, it should be clear that the invention may be used for monitoring and controlling body temperature in other procedures.

What is claimed is:

1. A hyperthermia system comprising:
   (a) means for drawing blood from a patient;
   (b) a heat exchanger for heating the drawn blood;
   (c) means for controlling the heating of the drawn blood comprising
      i) a catheter having:
         (a) an elongate body having a distal end and having a proximal end;
         (b) a first temperature sensor located proximate the distal tip; and
         (c) an inflatable cuff mounted distal of said first temperature sensor; and
      ii) a computer-based controller connected to said first temperature sensor and connected to said heat exchanger, such that said controller reads temperatures sensed by said sensor and adjusts the heat supplied by said heat exchanger in response thereto; and
   (d) means for returning the heated blood to the patient.

2. The hyperthermia system of claim 1, wherein said catheter further comprises: an evacuation lumen coextending through the elongate catheter body, coupled to a distal opening in said elongate body, whereby the contents of the bladder may be controlled by removal of urine or the infusion of saline into the bladder.

3. The hyperthermia system of claim 1 further comprising a second temperature sensor located in the urine pool by inflation of the cuff in use.

4. A hyperthermia system comprising:
   (a) a heat exchanger for heating drawn blood;
   (b) a catheter having:
      (i) an elongate body having a distal end and having a proximal end;
      (ii) a first temperature sensor located proximate the distal tip; and
      (iii) an inflatable cuff mounted distal of said first temperature sensor; and
   (c) a computer-based controller connected to said first temperature sensor and connected to said heat exchanger, such that said controller reads temperatures sensed by said sensor and adjusts the heat supplied by said heat exchanger in response thereto.

5. The hyperthermia system of claim 4, wherein said catheter further comprises: an evacuation lumen coextending through the elongate catheter body, coupled to a distal opening in said elongate body, whereby the contents of the bladder may be controlled by removal of urine or the infusion of saline into the bladder.

6. The hyperthermia system of claim 4, further comprising a second temperature sensor located in the urine pool by inflation of the cuff in use.

* * * * *